United States Patent
Klee et al.

(10) Patent No.: US 8,801,623 B2
(45) Date of Patent: Aug. 12, 2014

(54) SENSOR DETERMINING A PHYSICAL OR PHYSIOLOGICAL PARAMETER

(75) Inventors: Mareike Klee, Eindhoven (NL); Christianus Martinus Van Heesch, Eindhoven (NL); Dirk Jan Broer, Eindhoven (NL); Jacob Roger Haartsen, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 67 days.

(21) Appl. No.: 13/521,768

(22) PCT Filed: Jan. 10, 2011

(86) PCT No.: PCT/IB2011/050080
§ 371 (c)(1),
(2), (4) Date: Jul. 12, 2012

(87) PCT Pub. No.: WO2011/086481
PCT Pub. Date: Jul. 21, 2011

(65) Prior Publication Data
US 2012/0296224 A1    Nov. 22, 2012

(30) Foreign Application Priority Data
Jan. 14, 2010    (EP) .................................. 10150715

(51) Int. Cl.
*A61B 5/00* (2006.01)
*A61B 5/02* (2006.01)

(52) U.S. Cl.
USPC ........................... 600/504; 600/300; 600/505

(58) Field of Classification Search
USPC .................................. 600/300, 345, 504, 505
See application file for complete search history.

(56) References Cited

U.S. PATENT DOCUMENTS

| | | | |
|---|---|---|---|
| 4,926,875 A | 5/1990 | Rabinovitz et al. | |
| 6,296,622 B1 * | 10/2001 | Kurz et al. | 604/93.01 |
| 7,244,251 B2 | 7/2007 | Shehada et al. | |
| 2002/0099308 A1 * | 7/2002 | Bojan et al. | 600/573 |
| 2002/0128568 A1 | 9/2002 | Mooney et al. | |
| 2003/0195607 A1 * | 10/2003 | Trout et al. | 623/1.13 |
| 2004/0153008 A1 | 8/2004 | Sharf et al. | |
| 2005/0159673 A1 | 7/2005 | Dae et al. | |
| 2008/0045855 A1 | 2/2008 | Mooney et al. | |
| 2008/0091253 A1 | 4/2008 | Hammack et al. | |
| 2008/0176271 A1 * | 7/2008 | Silver et al. | 435/29 |
| 2008/0282791 A1 | 11/2008 | Nakano et al. | |

* cited by examiner

*Primary Examiner* — Michael D'Angelo
*Assistant Examiner* — Christian Jang

(57) ABSTRACT

A device and method determining or measuring a biological, physical or physiological parameter of an object includes a flexible carrier configured to be placed in a vicinity of the object; and at least one a sensor element attached to the flexible carrier and configured to determine at least one biological, physical or physiological parameter. In addition, a heating element is attached to the flexible carrier and configured to provide heat to the object; and a degradable adhesive is arranged on the flexible carrier adjacent to the heating element and configured to at least temporally affix the flexible carrier to the object.

16 Claims, 7 Drawing Sheets

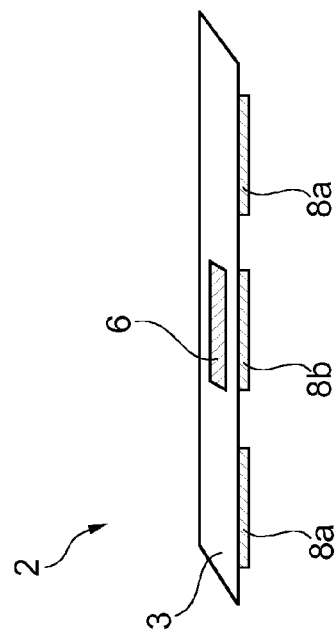
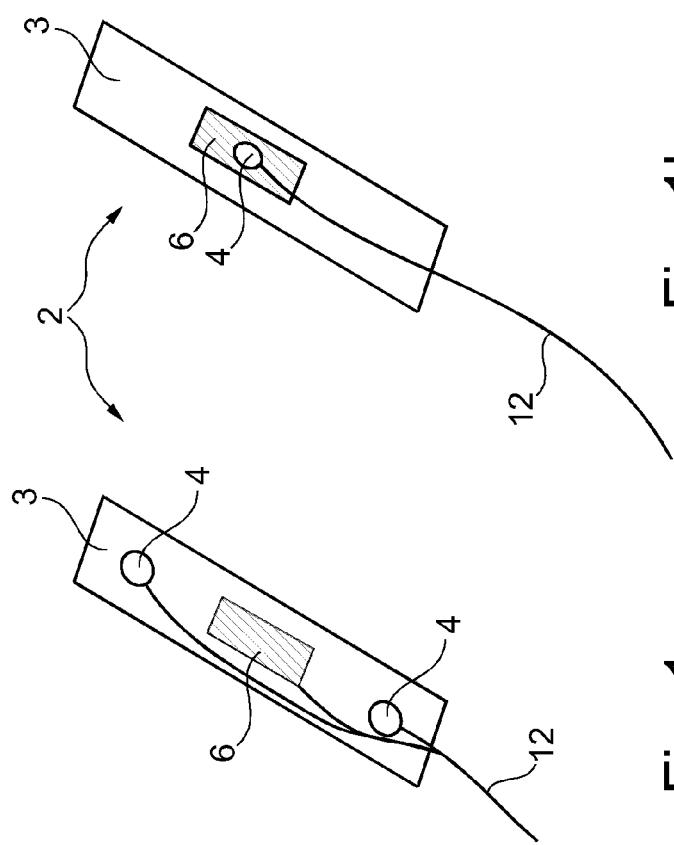

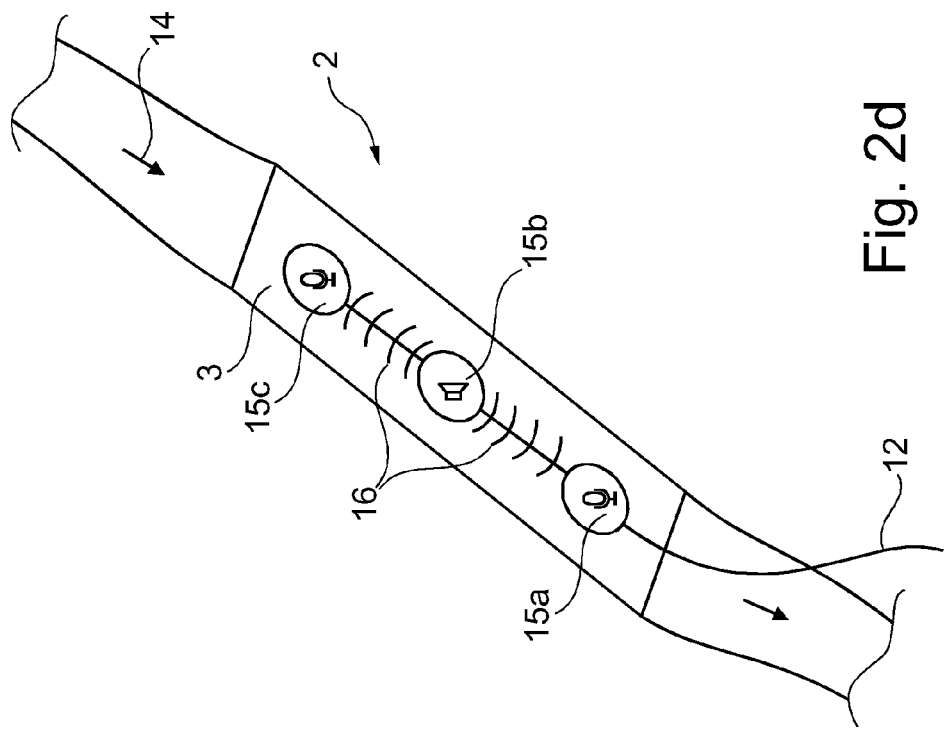
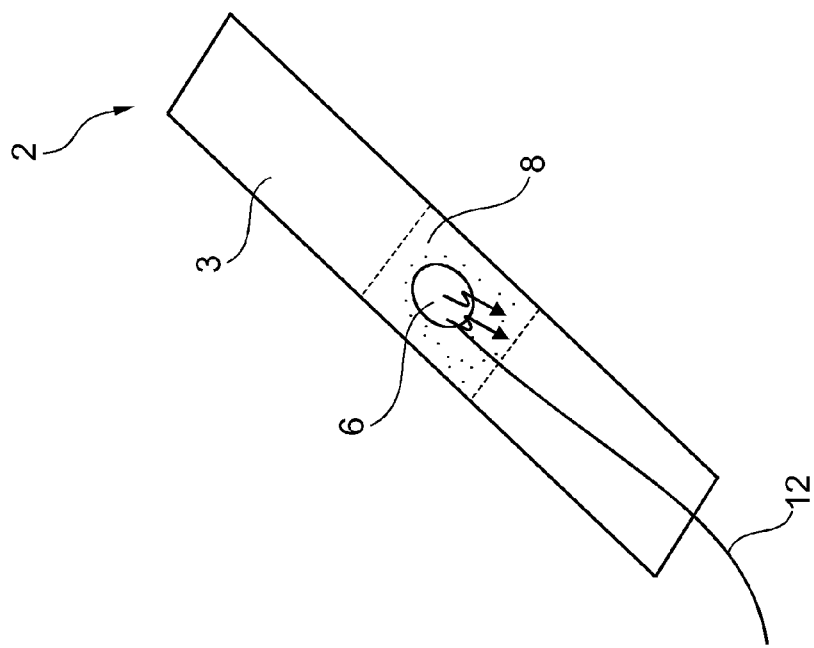

with n is 20 to 100.

SENSOR DETERMINING A PHYSICAL OR PHYSIOLOGICAL PARAMETER

FIELD OF THE INVENTION

The present invention relates to a sensor for determining a physical, biological or physiological parameter of an object to which the sensor is attached to, the sensor comprising a degradable adhesive.

The present invention also relates to the removal of the sensor from the object.

BACKGROUND OF THE INVENTION

After an installation of an object comprising a vessel-like or a pipe-like structure, for a subsequent passing of a fluid through the pipe structure or vessel structure, it may be beneficial to be able to determine whether there is a fluid flow present within the pipe-structure or vessel-structure as intended. E.g. when installing a pipe and subsequently connecting the pipe for obtaining a fluid flow, information whether the desired flow is present within the pipe-structure is beneficial for determining whether the installation was successful.

In the context of medical applications, for example after a transplantation procedure, medical personnel may be required to monitor a patient, in particular with regard to whether the patient's body is accepting a transplanted organ and/or whether the medical procedure was successful with regard to the transplantation itself, e.g., it may be required to monitor whether a transplanted organ is sufficiently circulated by bodily fluids. This may be done by determining from outside the body whether an object is fluid circulated, e.g. by determining its color or a by manual determination of fluid pulsation or fluid flow.

However, an according time to time manual check is a non-continuous monitoring procedure as well as comprises only an indirect manual determination thus a considerable risk remains that an according determination may be unsuccessful or that a non-flow condition may be detected too late for correction.

E.g. recognizing too late, that an implanted organ is not sufficiently circulated by fluid, may result in serious complications, e.g. even the abandonment of the organ by the host's body.

Thus, there may be a need for a sensor for determining a physical, biological or physiological parameter, in particular for continuously determining said parameter, which sensor furthermore may be easily removable, e.g. without an additional procedure.

Document U.S. Pat. No. 7,244,251 describes a surgical drain comprising a sensor for monitoring a condition of an anatomical side of fluid emitted from the side where the surgical drain is placed. The surgical drain is mechanically fixed to the anatomical side by an anchor element.

SUMMARY OF THE INVENTION

Accordingly, a sensor for determining a physical, biological or physiological parameter according to the independent claims is provided.

Preferred embodiments of the present invention may be derived from the dependent claims.

The present invention relates to monitoring or determining a physical, biological or physiological parameter like for example a temperature, e.g. a local temperature, or a further parameter, like a flow parameter of a fluid within a vessel of an object. The sensor may be attached to the object by a degradable adhesive and may be removed from the object by an induced degrading or a timed degrading of the degradable adhesive or a part thereof.

These and other aspects of the present invention will become apparent from and elucidated with reference to the embodiments described hereinafter.

Exemplary embodiments of the present invention will be described below with reference to the following drawings.

The illustration in the drawings is schematic. In different drawings, similar or identical elements are provided with similar or identical reference numerals.

The figures are not drawn to scale however may depict qualitative proportions.

BRIEF DESCRIPTION OF THE DRAWINGS

FIGS. 1$a$-$c$ show exemplary embodiments of a sensor for determining a biological or physiological parameter according to the present invention;

DETAILED DESCRIPTION OF THE EMBODIMENTS

Figure 2B:
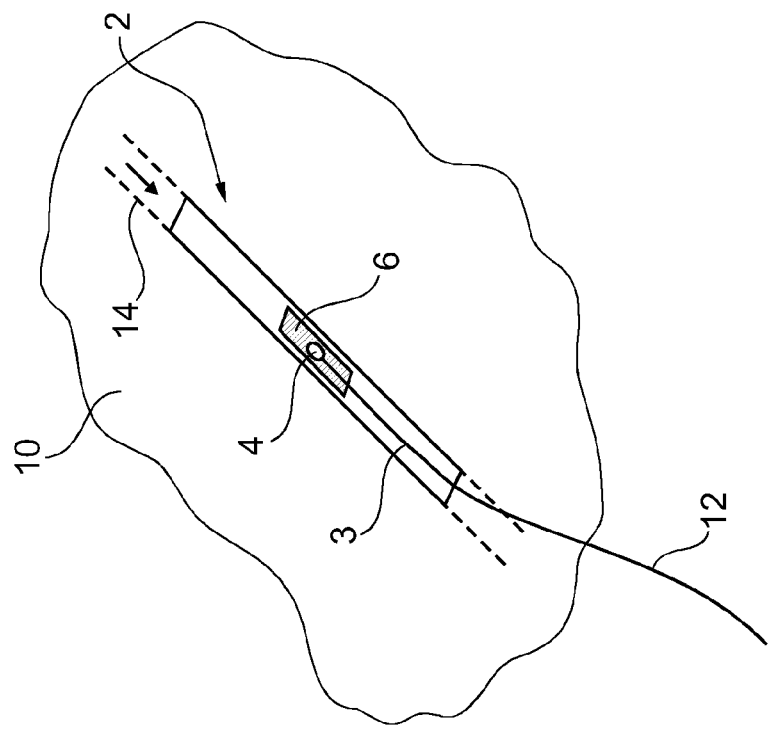
FIGS. 2$a$-$d$ show further exemplary embodiments of a sensor for determining a biological or physiological parameter according to the present invention.

The sensor according to the present invention may be employed for determining or measuring a biological, physical or physiological parameter, in particular of the object in the vicinity of the attachment region where the sensor is arranged at the object.

E.g., in case of a flow sensor, the sensor may be considered to constitute a thermal flow sensor. For example, an array of temperature determining elements, e.g. thermocouples, in particular e.g. two, four, six, eight or more temperature determining elements, may be located at defined positions within a heating element in the center or middle between the temperature determining elements, in particular with one half of the number of temperature determining elements on each side of the heating element, for example linearly arranged.

The sensor may be attached to an object or a vessel and within the object or vessel, a fluid may be arranged. The sensor may be employed for determining a flow within the fluid, e.g. water within a pipe or blood within a blood-vessel. The heating element may constitute a heat source for locally heating the object. Depending on a flow velocity of the fluid in a vessel, a temperature may be induced to the object and thus the fluid, with temperature determining elements adapted for determining a local temperature of the object, which temperature determining elements are located upstream and downstream of the heating element. The temperature determining elements may determine a local temperature, which may be compared for determining a temperature difference. An according temperature difference may indicate a fluid flow within the vessel.

In case there is no substantial temperature difference between the temperature determining elements located upstream and downstream of the heating element, a condition with no fluid flow may be assumed within a vessel. On the other hand, in case there is a temperature difference, a fluid flow may be assumed.

Also by employing temperature determining elements both upstream and downstream of the heating element, a flow direction may be determined. E.g. in case there is a temperature difference determinable with temperature determining elements located upstream and downstream of the heating element, since a heat source is provided to the fluid within the vessel by the heating element, the temperature determining element that determines an increased temperature versus a further temperature determining element on the other side of the heating element, which may determine a lesser temperature, may be considered to be downstream of the heating element with respect to a flow direction within the vessel.

Also, a fluid flow within a vessel may be determined by measuring a flow dependent cooling of the heating element using temperature determining elements such as thermocouples, resistors or transistors. In this case, a single sensor element e.g. a single temperature determining elements or thermocouple, may be arranged in the vicinity of the heating element.

A certain amount of energy may be applied to the heating element, possibly defining a supposed resulting temperature of the heating element. In case the thermocouple arranged in the vicinity of the heating element is determining a temperature different from the temperature the heating element is supposed to comprise due to the supplied energy, a fluid flow may be indicated. The amount of fluid flow may be directly related to the amount of temperature difference between the supposed temperature the heating element should have due to the energy provided and the actual measured temperature of the heating element by the sensor element.

An according method may be more robust with regard to variations in the wall thickness of a vessel containing the fluid. Preferably, the sensor in particular the heating element may be operated in a constant temperature mode for avoiding excessive heating of both the object the sensor is attached to and the fluid within the vessel.

E.g., the heating element and the at least one sensor element may be provided with a feedback loop for maintaining the temperature of the heating element at a constant pre-set value. The power dissipating in the heating element to maintain the constant temperature level may be a measure for the flow of a fluid within the vessel. Also, in a constant temperature mode, an overheating may be controlled, thus avoided, e.g. for avoiding unwanted premature degradation of a degradable adhesive, which degradable adhesive may be a temperature degrading adhesive.

Furthermore, a fluid flow may be determined by the "time-of-flight" of a heat pulse provided by the heating element to the object and/or the vessel, which heat pulse may be determined by a sensor element located spaced apart from the heating element, e.g. again up- and downstream of the heating element with respect to the vessel of the object the sensor is attached to.

E.g., a heat pulse is provided to the object and thus the vessel, which heat pulse is subsequently determined at one sensor element only of at least two sensor elements located upstream and downstream of the heating element, a fluid flow may be assumed and also a flow direction may be determinable. In case no temperature difference between the at least two sensor elements located upstream and downstream of the heating element or even no temperature change at all may be determinable by the sensor element, a non-flow situation may be assumed.

The sensor for determining a biological, physical or physiological parameter may be attached to the object and/or the vessel by a degradable adhesive. The sensor may preferably be flexible for attachment to a flexible object or vessel, e.g. by employing circonflex technology, e.g. for fabrication of sensors on a biocompatible flexible carrier like parylene. Further, the sensor may be provided with a biocompatible layer like poly(chloro-p-xylylene) (Parylene C) or poly(p-xylylene) (Parylene N) or poly-dimethylsiloxane (PDMS).

The determined or measured parameter may be transferred to a monitoring unit, e.g. for continuously monitoring the parameter either by a wired connection or by a wireless connection. The sensor may also comprise anti-biofouling agents, e.g. silver, in particular silver particles.

For attachment of the sensor to the object, a biodegradable adhesive may be employed, e.g. comprising a mixture of degradable thiol monomers, non-degradable thiol monomers and polyethylene glycol-diallyl ether. Also, the sensor may be attached to the object by employing as adhesive a polymer such as acrylate polymers, e.g. poly(glycerolcosebacate)-acrylate with enzymes induced. With induced enzymes, the polymer may be biodegradable so that after a defined period, e.g. days to weeks, the sensor may be detaching itself from the object by degrading the adhesive characteristics of the degradable adhesive.

Also, the sensor may be attached to the object by a biodegradable adhesive such as lactate. A controlled degradation of the adhesive may be provided by the heating element or a further heater element integrated in the sensor, in particular in the area of the degradable adhesive.

In particular, a two-layer adhesive may be employed. First, the sensor may be provided with a removable element or removable coating or a degradable element or degradable coating, for example a hot melt coating, e.g. based on an ethylene-vinyl acetate (EVA) copolymer modified with a tackifyer, e.g. a wax or hot melt wax, to optimize its melting temperature, which may be preferably below 80° C. The adhesion of the coated sensor to the object may employ an adhesive as described earlier. In case the sensor is to be detached from the object, the removable component may for example be melted, e.g. by heating the sensor by the heating element or the further heater element. A remaining adhesive component or adhesive element, e.g. a thiol-ene adhesive, may remain attached to the object or vessel, however may bio-degrade slowly afterwards.

The hot melt component may also be heated employing a laser source as a heating element or a heater element, in particular while employing a dye material adapted for a preferred absorption of laser energy of a particular wavelength emitted by the laser element for conversion into heat. Accordingly, the laser source may be considered to be a heating element or heater element for providing heat for melting the hot melt component of the degradable adhesive.

Furthermore, instead of providing a heating element and at least one sensor element for determining a temperature, also a sound transducing element, in particular an ultrasound transducing element, i.e. an element adapted for both emitting and receiving acoustic waves, or dedicated sound generating and sound receiving elements, as the at least one sensor element, adapted for determining a sound pressure level and/or a frequency, may be employed.

E.g., an acoustic transducer or ultrasound transducer may be provided instead of or with the heating element or heater element. Further acoustic transducers may be arranged as sensor elements, thus an array of acoustic transducer elements, e.g. two or three acoustic transducer elements, may be employed for determining a flow parameter. For example by employing two acoustic transducers, one acoustic transducer may emit an acoustic pulse with the other acoustic transducer receiving the acoustic pulse, e.g. an ultrasound pulse. Accordingly, a time of flight and frequency or frequency difference between the emitted and received acoustic pulses may be determinable. The array of two acoustic transducers may subsequently reverse their individual operation mode, thus the transducer previously employed for providing the acoustic pulse may now determine a time of flight, intensity and/or frequency of an acoustic pulse emanated from the respective other transducer element. In case there is a time of flight difference or frequency difference between the individual modes of operation, a fluid flow may be assumed as well as a flow direction in accordance with the physical principle of the Doppler effect.

The transducer or the array of transducers may also be used to operate as transmitting element(s) and receiving element(s) of the sound pulses, in particular ultrasound pulses. In case one transducer or an array of transducer is located at one position and one transducer or an array transducer is located at another position, the time between transmitting the ultrasound pulse and receiving the ultrasound pulse, i.e. the time of flight, may be $t_0$ in case there is no fluid flow, depending on the distance between the transducers or the transducer arrays. In case a time $t_1$ between transmitting the ultrasound pulse and receiving the ultrasound pulse is $t_1 > t_0$ or $t_1 < t_0$, a fluid flow may be assumed as well as a fluid flow direction detected.

In case an array of at least three acoustic transducers is employed, the center transducer may provide an acoustic pulse, which acoustic pulse is subsequently determined or detected by both transducer elements located upstream and downstream of the central transducer. Again, by employing the Doppler effect or determining the time of flight, a fluid flow may be determinable as well as a flow direction, however in this case with only one acoustic pulse provided.

In case it is decided that the sensor is to be detached from the object, the degradable adhesive may be intentionally degraded by induced degradation, e.g. by heat, and the sensor may be removed by pushing or pulling it out, e.g. employing wires attached to the sensor element for a wired connection.

Now referring to FIGS. 1a-1c, exemplary embodiments of a sensor for determining a biological, physical or physiological parameter according to the present invention are depicted.

FIG. 1a shows an exemplary embodiment of a sensor 2 comprising two sensor elements 4 as well as a heating element 6 arranged in between the sensor elements 4. Both the sensor elements 4 and the heating element 6 are arranged on a flexible carrier element 3, e.g. employing the circonflex technology. Both sensor elements 4 as well as the heating element 6 are connected employing wire 12 for providing energy to the heating element 6 as well as for receiving a determined physiological, physical or biological parameter, e.g. a local temperature, by each of the sensor elements 4. Wire 12 may be connected to an external unit for controlling the sensor 2, in particular heating element 6, as well as for analyzing information received from sensor elements 4.

Now referring to FIG. 1b, a further exemplary embodiment of a sensor 2 is depicted.

Sensor 2 of FIG. 1b comprises again heating element 6 and a single sensor element 4 arranged in the vicinity or within heating element 6. A wire 12 is connecting both the heating element 6 and the sensor element 4 with an external unit, which is not depicted. By employing sensor element 4, a cooling of heating element 6 may be determinable, and thus a fluid flow within an object to which sensor 2 may be attached to.

Now referring to FIG. 1c, possible locations of a degradable adhesive 8a,b according to an exemplary embodiment of the present invention is depicted.

Attached to one side of carrier element 3, three areas of a degradable adhesive 8a,b are depicted. Degradable adhesive 8b is arranged in the vicinity of heating element 6 while two areas of degradable adhesive 8a are arranged on either side of heating element 6 on the opposing side of carrier element 3. It may be also be conceivable to omit degradable adhesive element 8a completely, thus attaching the sensor to an object only employing degradable adhesive 8b. By employing heating element 6 or a further heater element, a possible heat degradable adhesive 8b or a hot melt degradable adhesive 8b may be influenced such that the adhesive characteristics of the degradable adhesive 8b are altered so that a detachment of the sensor 2 from an object may be achievable.

Now referring to FIGS. 2a-d, further exemplary embodiments of a sensor for determining a biological, physical or physiological parameter according to the present invention are depicted.

Figure 2A:
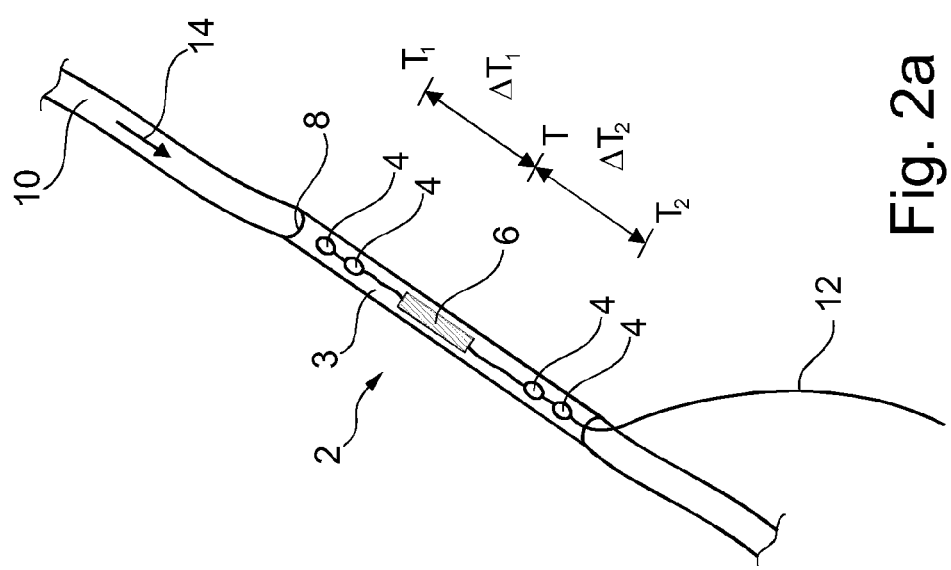

In FIG. 2a, sensor 2 is arranged in the vicinity of object 10, exemplarily a vessel 10, as depicted in FIG. 2a. The carrier element is preferably round or convex, e.g. vessel shaped for attaching sensor 2 to object 10. Sensor 2 in FIG. 2a exemplarily comprises four sensor elements 4 arranged in two pairs on each side of heating element 6, one pair arranged upstream and one pair arranged downstream of heating element 6 with regard to a flow of a fluid 14 within vessel 10. However, it may also be conceivable to employ only two sensor elements 4, one on each side of heating element 6, as depicted in FIG. 1a.

Heating element 6 may be adapted to provide a temperature T to object 10 in the vicinity of heating element 6. Thus, heating element 6 may be considered to be heating object 10 to temperature T or at least employing temperature T. Accordingly, by sensor elements 4, a temperature, in particular a local temperature $T_1$ and/or $T_2$ may be determinable and thus a temperature difference $\Delta T_1$ as well as $\Delta T_2$ between the temperature of the heating element 6 and the respective sensor elements 4. In case $T_1$ substantially equals $T_2$, thus $\Delta T_1$ equals $\Delta T_2$, a non-flow condition within vessel 10 may be assumed. In case e.g. $T_2$ is larger than $T_1$, possibly nearing or equaling T, a fluid flow 14 may be assumed within vessel 10. E.g., in case $T_2$ is larger than $T_1$, a flow 14 from heating element 6 in the direction of the sensor elements measuring the higher temperature $T_2$, thus, with regard to FIG. 2a, a flow from top to bottom may be assumed.

With regard to FIG. 2b, sensor 2 is attached to object 10 comprising a vessel in which vicinity sensor 2 is attached to object 10. In FIG. 2b exemplary a sensor element in accordance with FIG. 1b is employed. However, as with all exemplary embodiments described herein, all sensors described may be employed equally.

By wire 12, energy may be provided to heating element 6 for generating a constant temperature. In case vessel 10, to which sensor 2 is attached to, comprises a fluid flow 14, a cooling of heating element 6 may occur, which cooling or temperature difference may be determinable by sensor element 4, arranged in a vicinity of heating element 6. E.g. in case a fluid flow 14 is present in object 10, heating element 6 may be cooled more than would be the case if no fluid flow 14 is present within object 10. Thus, e.g. by providing a constant temperature via heating element 6, sensor element 4 may determine a temperature, which is smaller than a temperature in case no fluid flow 14 would be present.

In FIG. 2c, heating element 6 is embodied as a laser source. Energy for producing laser light of a defined wavelength is provided by wire 12. Degradable adhesive 8 may comprise a dye that is adapted to the wavelength of laser source 6 for a preferred absorption of laser energy and thus heating of the degradable adhesive 8.

Thus, in case of a hot melt degradable adhesive 8, heating element 6 incorporated as a laser source 6, may heat the degradable adhesive such that it may be detached from an object 10, not depicted in FIG. 2c. In FIG. 2c the laser source 6 and the heating element 6 are substantially identical elements. However, it may also be conceivable that sensor 2 comprises a heating element 6 as well as a further laser source both of which may be operated independently by wire 12. Also, laser source 6 may be adapted for providing light at at least two different wavelengths. One wavelength may be adapted to a dye of the degradable adhesive 8 for removal of the sensor, thus an operation as a heater element, while a further wavelength may be employed for an operation as a heating element, thus for the heating of object 10.

In FIG. 2d, an implementation of sensor 2 comprising acoustic transducers is depicted. In FIG. 2d exemplary three acoustic transducers 15a-15c, e.g. ultrasound transducer, are depicted. In FIG. 2d exemplary acoustic transducer 15b is adapted for emanating ultrasound, while acoustic transducers 15a and 15c are adapted for receiving acoustic sound waves 16 emanating from acoustic transducer 15b.

Sound emanating from acoustic transducer 15b may comprise a defined wavelength. In case a fluid flow 14 is present, due to the physical principle of the Doppler effect, the frequency of the received acoustic wave by transducer 15a may be larger than the frequency of emitted acoustic wave from transducer 15b, which again may be larger than the frequency received by transducer 15c. Accordingly, by a frequency difference, a fluid flow 14 as well as the direction of fluid flow 14 and also a fluid flow velocity, may be determinable. Sensor 2 may also only comprise two acoustic transducers 15a, 15b in a dual reverse configuration, e.g. requiring both acoustic transducers to emanate an acoustic wave consecutively with the respective other acoustic transducer receiving the acoustic wave. In case there is a frequency difference between the received frequencies, a flow of fluid 14 as well as the direction and velocity may be determined.

Figure 3A:
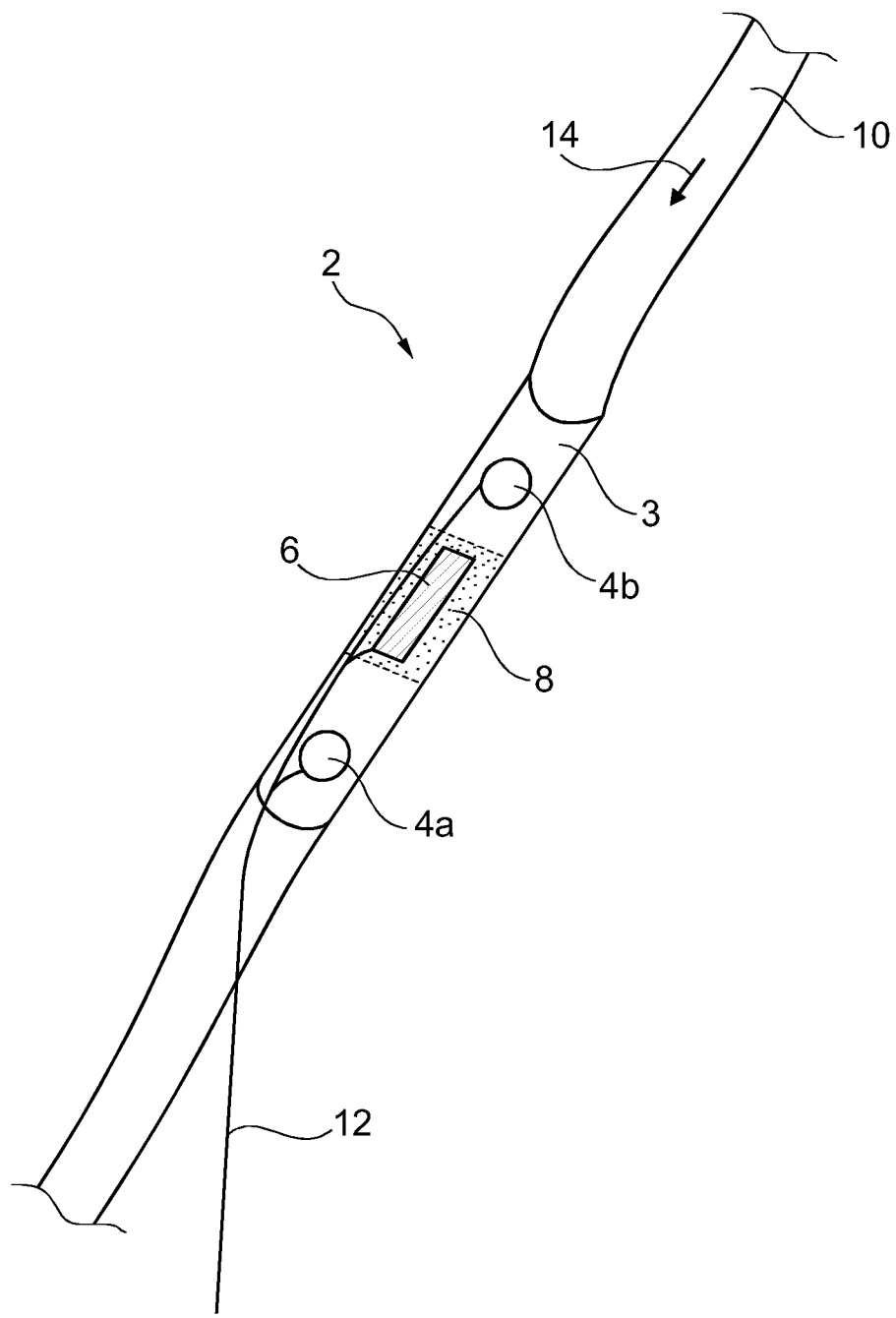
FIGS. 3$a$-$c$ show an exemplary embodiment of determining a fluid flow employing a heat pulse according to the present invention.
Figure 3B:
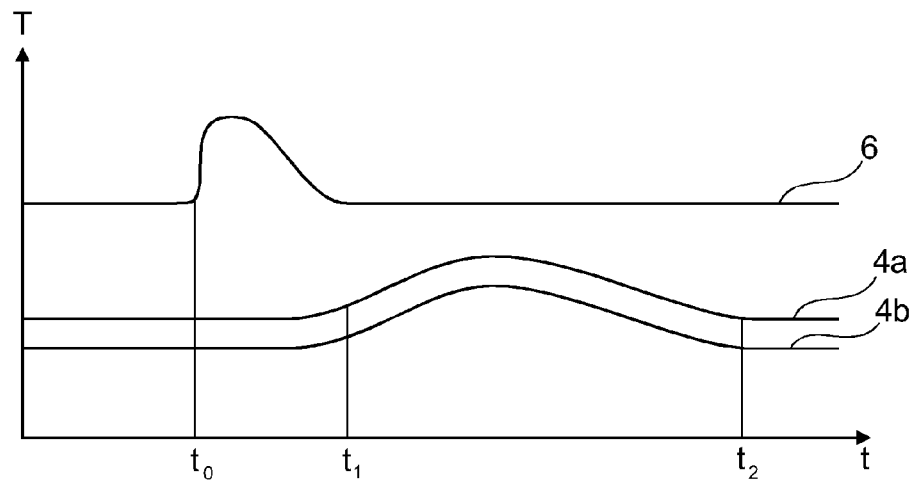
Figure 3C:
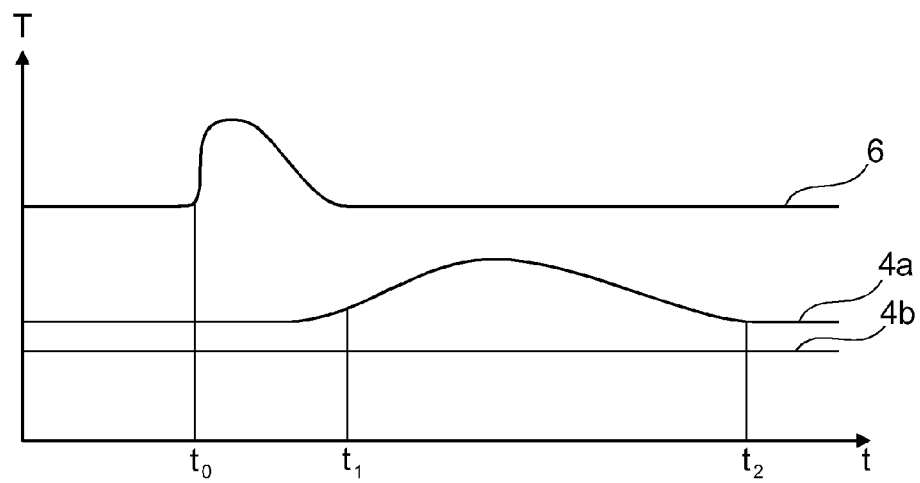

Now referring to FIGS. 3a-c, an exemplary embodiment of determining a fluid flow employing a heat pulse according to the present invention is depicted.

In FIG. 3a, substantially a sensor 2 according to FIG. 1a is attached to a vessel 10 employing a degradable adhesive 8. Sensor 2 comprises two sensor elements 4a,b arranged upstream and downstream with regard to a possible fluid flow 14 within vessel 10. Heating element 6 may provide a temperature pulse, thus a sudden increase in temperature, which may be substantially temporary or also a long-term increase, with the sensor elements 4a,b subsequently determining a possible temperature increase within their field of measurement, thus a possible local temperature increase.

With regard to FIG. 3b, which depicts a no flow scenario, a heat pulse is provided by heating element 6 at time $t_0$. Subsequently at time $t_1$ both sensor elements 4a,b determine an increase in temperature lasting until $t_2$. Accordingly, the temperature pulse provided by heating element 6 may be considered to spread uniformly in both directions towards sensor element 4a as well as 4b. Thus, it may be assumed that no fluid flow 14 is present within vessel 10.

With regard to FIG. 3c, only one sensor element, here sensor element 4a, is detecting a temperature increase at $t_1$. Temperature increase $T_1$ is only to be determined at sensor element 4a, thus indicating a fluid flow 14 in the direction from sensor element 4b to heating element 6 to sensor element 4a within vessel 10.

Now referring to FIGS. 4a-4d, exemplary embodiments of components of a degradable adhesive according to the present invention are depicted.

Figure 4A:
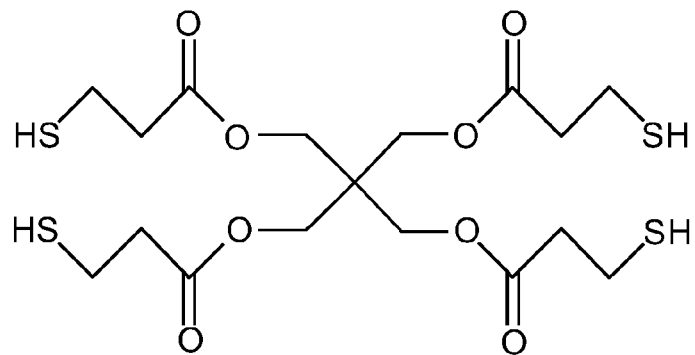
FIGS. 4$a$-$d$ show exemplary embodiments of components of a degradable adhesive according to the present invention.
Figure 4B:
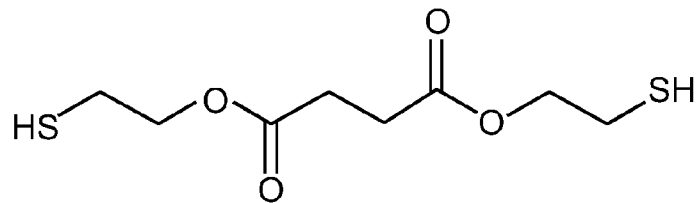
Figure 4C:
Figure 4D:
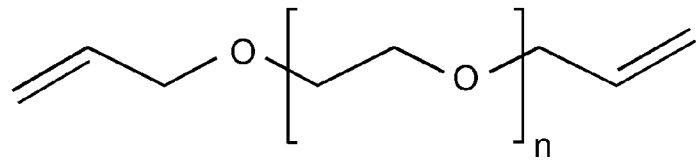

FIG. 4a depicts an example of a degradable tetrathiol, pentaerythritol tetrakis(3-mercaptopropionate), FIG. 4b depicts an example of a degradable dithiol, glycol dimercaptopropionate, FIG. 4c depicts an example of a non-degradable dithiol, 2,2'-(ethylenedioxy) diethanediol and FIG. 4d depicts an example of a polyethylene glycol diallyl ether.

The monomers may be mixed in a molar concentration of allyl groups and thiol groups, which are equal. A ratio between a degradable and a non-degradable thiol may determine the degradation rate of an adhesive, which may be, after curing of the adhesive, between 1 and 25 days for 0 mol-% and 15 mol-% of non-degradable thiols, respectively.

For curing, a small amount of initiator needs to be added, typically 0.2 wt-% 1-[4-(2-hydroxyethoxy)-phenyl]-2-hydroxy-2-methyl-1-propane-1-one (Irgacure 2959—CIBA). The adhesive may be a liquid at room temperature and may be cured by 100 s exposure to UV light using a waveguided 365 nm mercury lamp with $$\frac{100 \text{ mW}}{\text{cm}^2}.$$

Figure 5:
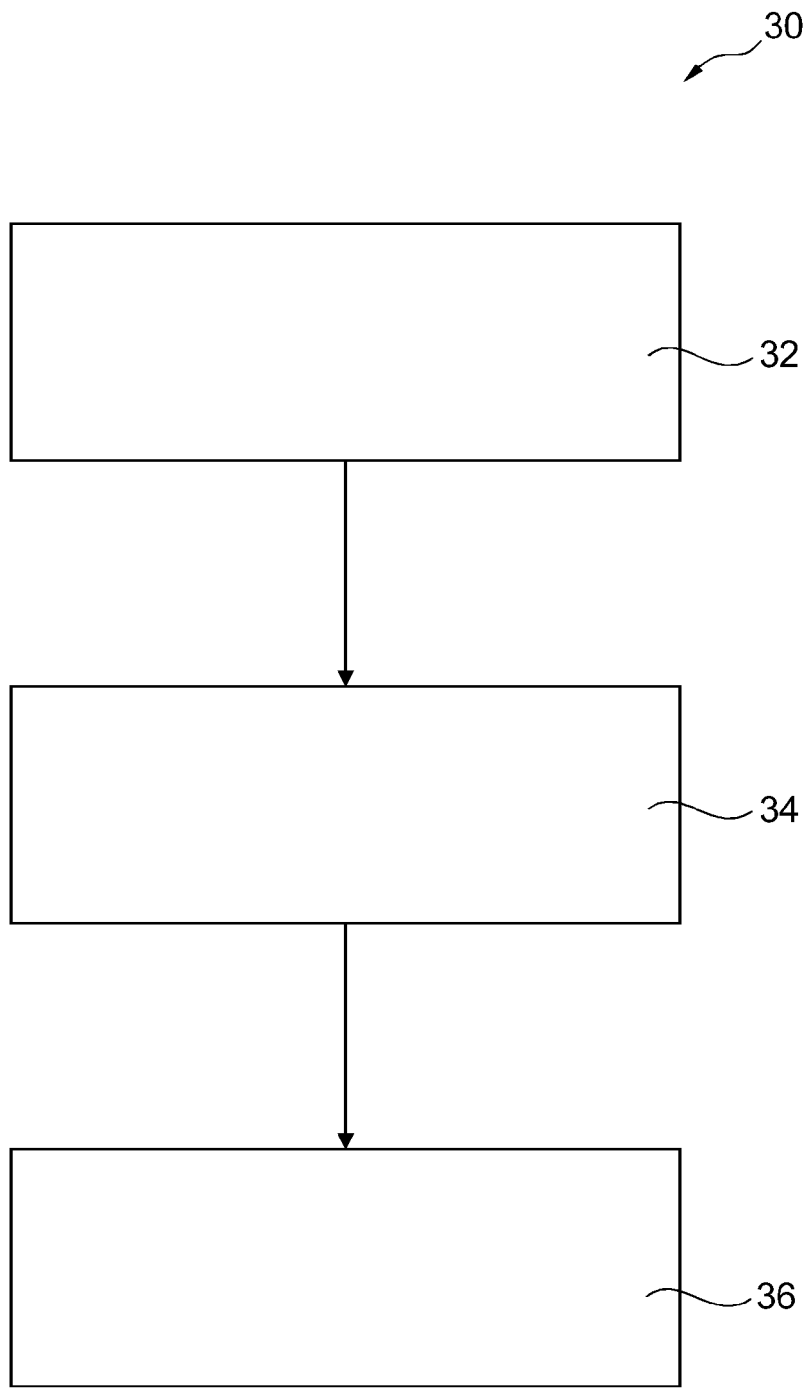
FIG. 5 shows an exemplary embodiment of a method of removing a sensor from an object according to the present invention.

Now referring to FIG. 5, an exemplary embodiment of a method of removing a sensor from an object according to the present invention is depicted.

FIG. 5 shows a method 30 for removing a sensor from an object comprising employing 32 a heating element 6 for providing a heat source, wherein the heat source is adapted for degrading a degradable adhesive 8. A sensor 2 according to the present invention is detached 34 from an object 10 by the degradation of the degradable adhesive 8. The sensor 2 is subsequently removed 36 from the object 10, e.g. by pulling sensor 2, employing wire 12.

It should be noted that the term "comprising" does not exclude other elements or steps and that "a" or "an" does not exclude a plurality. Also, elements described in association with different embodiments may be combined.

It should also be noted, that reference numerals in the claims shall not be construed as limiting the scope of the claims.

| LIST OF REFERENCE NUMERALS: | |
|---|---|
| 2 | Sensor |
| 3 | Carrier element |
| 4a, b | Sensor element |
| 6 | Heating element/laser source |
| 8a, b | Degradable adhesive |
| 10 | Object/vessel |
| 12 | Wire |
| 14 | Flow of fluid |
| 15a-c | Ultrasound transducer |
| 16 | Sound waves |
| 30 | Method of removing a sensor from an object |
| 32 | STEP: employing a heating element |
| 34 | STEP: detaching a sensor from an object |
| 36 | STEP: removing the sensor. |

The invention claimed is:

1. A device for determining a biological, physical or physiological parameter of an object, the device comprising:
   a flexible carrier configured to be placed in a vicinity of the object;

at least one sensor element attached to the flexible carrier and configured to determine at least one biological, physical or physiological parameter;

a heating element attached to the flexible carrier and configured to provide heat to the object; and a degradable adhesive arranged on the flexible carrier adjacent to the heating element and configured to at least temporally affix the flexible carrier to the object.

2. The device according to claim 1, wherein the sensor element comprises at least one of a flow sensor element, a pressure sensor element, a temperature sensor element, a chemical compound sensor element, a thermocouples element, an ultrasound element, a resistor element and a transistor element.

3. The device according to claim 1, wherein the sensor is configured to transmit the at least one biological, physical or physiological parameter in a manner selected from one of a wired transmission and a wireless transmission.

4. The device according to claim 1, wherein the degradable adhesive comprises an adhesive element and a degradable element.

5. The device according to claim 4, wherein the heat from the heating element degrades the degradable element.

6. The device according to claim 5, wherein the heating element is a laser element configured to emit radiation of a first wavelength.

7. The device according to claim 6, wherein the degradable element is released by the radiation of the first wavelength.

8. The device according to claim 1, further comprising a link for providing power to the heating element and for retrieving the at least one parameter.

9. The device according to claim 5, wherein the link comprises first and second acoustic transducers, the second acoustic transducers receiving ultrasound waves emanating from the first acoustic transducer.

10. The device according to claim 1, wherein the sensor element is arranged at the heating element for determining one of a temperature of the heating element and/or the object, a temperature difference of the heating element and/or the object and a cooling of the heating element and/or the object.

11. The device according to claim 1, wherein the sensor element is arranged at a distance from the heating element; and configured to provide a heat pulse to the object and to determine a local temperature of the object.

12. The device according to claim 1, further comprising at least two sensor elements configured to determine a local temperature of the object, wherein the heating element is arranged between and is spaced apart from the at least two sensor elements.

13. The device according to claim 1, wherein the degradable element is at least one of a biodegradable adhesive, a temperature degradable adhesive, a chemical degradable adhesive and an enzyme degradable adhesive.

14. The device according to claim 1, further comprising at least one of a biocompatible element, a biocompatible layer, a biocompatible coating, an anti-biofouling material, silver and silver particles.

15. The device according to claim 1, wherein the a biological, physical or physiological parameter is from a blood flow parameter of the object.

16. A method of removing a device from an object, comprising acts of:

providing a device including a flexible carrier for placing in a vicinity of the object and having at least one sensor element for determining at least one biological, physical or physiological parameter, a heating element for providing heat to the object, a link for providing power to the sensor element and receiving the parameter, and a degradable adhesive adjacent to the heating element for affixing the flexible carrier to the object;

controlling the heating element to provide heat to the object and degrading the degradable adhesive;

wherein the degradable adhesive includes an adhesive element and a degradable element and degrading of the degradable adhesive degrades the degradable element causing detaching of the device from the object.

* * * * *